United States Patent [19]

Shalaby et al.

[11] Patent Number: 5,824,411
[45] Date of Patent: Oct. 20, 1998

[54] SELF-REINFORCED ULTRA-HIGH MOLECULAR WEIGHT POLYETHYLENE COMPOSITES

[75] Inventors: Shalaby W. Shalaby, Anderson; Meng Deng, Clemson, both of S.C.

[73] Assignee: Poly-Med, Inc., Pendleton, S.C.

[21] Appl. No.: 480,848

[22] Filed: Jun. 7, 1995

Related U.S. Application Data

[62] Division of Ser. No. 110,155, Aug. 20, 1993, abandoned.
[51] Int. Cl.$^6$ ..................................................... D02G 3/32
[52] U.S. Cl. .......................... 428/364; 428/373; 428/397; 428/500; 428/902; 623/11; 623/18; 623/23; 264/138; 264/163; 264/322; 264/323
[58] Field of Search ..................................... 428/364, 373, 428/902, 397, 500; 264/138, 163, 322, 323; 627/18, 23, 11

[56] References Cited

U.S. PATENT DOCUMENTS

| | | | |
|---|---|---|---|
| 4,055,862 | 11/1977 | Fatling | 3/1.95 |
| 4,610,688 | 9/1986 | Silvestrini et al. | 623/1 |
| 5,030,402 | 7/1991 | Zacharaides | 264/138 |
| 5,064,439 | 11/1991 | Chang et al. | 623/66 |
| 5,395,691 | 3/1995 | Kavesh et al. | 428/357 |

FOREIGN PATENT DOCUMENTS

| | | |
|---|---|---|
| 83101731 | 12/1983 | European Pat. Off. . |
| PCT/US92/10005 | 6/1993 | WIPO . |

OTHER PUBLICATIONS

Stern, et al., "Wear properties of retrieved carbon–reinforced and UHMW–PE tibial components," Ultra–High Molecular Weight Polyethylene as Biomaterial in Orthopedic Surgery, H.G. Willert, G.H. Buchhorn, and P. Eyerer, eds., Hogrefe & Huber Publishers (1991), pp. 258–261.

Wright, et al., "Carbon fiber–reinforced UHMWPE for total joint replacement components," Composites in BioMedical Engineering, 1st International Conference 1985, pp. 21/1–21/4.

Mead, et al., "The preparation and tensile properties of polyethylene composites," J. Applied Polymer Science, 22:3249–65 (1978).

Hirte, et al., "A one polymer composite polyethylene film: failure morphology," Morphology of Polymers, Walter de Guyter & Co., 1986, pp. 527–539.

Ishida, H. and Bussi, P., "Surface–induced crystallization in ultrahigh modulus polyethylene fiber reinforced polyethlene composites," Macromolecules, 24:3569–77 (1991).

Deng, et al., "Thermal and thermo–oxidation properties of Virgin UHMW–PE," The 19th Annual Meeting of the Society for Biomaterials, Apr. 28–May 2, 1993, Birmingham, Alabama.

Ciferri, A. and Ward, I.M., "Ultra–High Modulus Polymers," Applied science Publishers, Ltd., England 1979, pp. 70–75.

(List continued on next page.)

Primary Examiner—Richard Weisberger
Attorney, Agent, or Firm—Leigh P. Gregory

[57] ABSTRACT

The invention provides composites of ultra-high molecular weight polyethylene reinforced with ultra-high molecular weight polyethylene anisotropic reinforcement of high strength and modulus. The composites have superior mechanical properties relative to non-filled ultra-high molecular weight polyethylene, including higher strength, impact strength, increased creep resistance, and improved modulus. The composites may be sterilized for biomedical use, using gamma radiation and other techniques. Further, the composites are resistant to the effect of body fluids and have lower creep rates so that they will provide implant life. The composites may be cross-linked by exposure to an acetylene environment. Also, the composites find use in other high strength, high impact applications such as sports equipment.

7 Claims, 9 Drawing Sheets

OTHER PUBLICATIONS

McKenna, et al., "Mechanical properties of some fibre reinforced polymer composites after implantation as fracture fixation plates," Biomaterials 1980, vol. 1, IPC Business Press (1980), pp. 189–192.

Soltsz, U. and Richter, H., "Investigation of Mechanical behavior of Fibre–reinforced Materials for Endoprosthetic Devices," Biomaterials 1982, G.D. Winter, Gibbons, and H. Pienk, Jr., eds., (1982), pp. 33–38.

Bradley, J.S. and Hastings, G.W., "Carbon Fibre–Reinforced Plastics for Orthopaedic Implants," Mechanical Properties of Biomaterials, G.W. Hastings and D.F. Williams, eds., John Wiley & Sons Ltd. (1980), pp. 379–386.

Grobbelaar, C.J., et al., "The Radiation Improvement of Polyethylene Prostheses: A Preliminary Study,"The Journal of Bone and Joint Surgery, vol. 60, No. 3 (Aug. 1978), pp. 370–374.

Wright, et al., "The effect of carbon fiber reinforcement on contact area, contact pressure, and time–dependent deformation in polyethylene tibial components," J. of Biomedical Materials & Research, vol. 15, pp. 719–730 (1981).

Connelly, et al., "Fatigue Crack Propagation behavior of Ultrahigh Molecular Weight Polyethylene," J. of Orthopedic Research, vol. 2, No. 2, Raven Press (1984), pp. 119–125.

Deng, M. and Shalaby, W., "Determinants of Thermal Events in Ultrahigh molecular Weight Polyethylene," Polymers for Advanced Technologies, vol. 4 (1993), pp. 43–46.

Wright, T. M., et al., "Analysis of Surface Damage in Retrieved Carbon Fiber–Reinforced and Plain Polyethylene tibial Components from Posterior Stabilized Total Knee Replacements," The Journal of Bone and Joint Surgery, vol. 70–A, No. 9, (Oct. 1988), pp. 1312–1319.

SELF-REINFORCED ULTRA-HIGH MOLECULAR WEIGHT POLYETHYLENE COMPOSITES

This is a division of U.S. patent application Ser. No. 08/110,155 filed Aug. 20, 1993, now abandoned.

BACKGROUND OF THE INVENTION

1. Field of the Invention

The invention relates to novel composites of ultra-high molecular weight polyethylene (UHMWPE) self-reinforced by high strength and modulus fibers of UHMWPE, and methods for composite production and sterilization for biomedical use. The composite has superior mechanical properties which allows its use in applications where high strength, creep resistance, and impact resistance are important, such as sports equipment, protective equipment, medical implants, external prostheses, medical appliance components, and the like.

2. Description of the Related Art

A major application of ultra-high molecular weight polyethylene (UHMWPE) in medical devices is its use as load-bearing components of articulating joint prostheses, such as hip and knee prostheses. As this type of surgery is applied to younger patients and a longer implant-life span is expected, the failure of prostheses to function, due to cold flow (creep) of UHMWPE, becomes important. In the past, attempts were made to improve the long term performance (wear and creep resistance) of UHMWPE without significant success. Amongst the most-explored approaches to control the UHMWPE creep was its reinforcement with carbon fibers. It was assumed that increased creep resistance would also benefit the wear property of the polymer. However, analytical and clinical studies of carbon fiber reinforced UHMWPE composites, as used in components for total joint replacement, have shown no advantage in using such composite materials in place of non-filled UHMWPE. In fact, the wear characteristics of the composite were inferior to those of the non-filled polymer: both coefficient of friction and wear rate increased. Fatigue crack propagation resistance was found to be significantly worse in the composite than in UHMWPE. These results were attributed to: (1) brittle nature of carbon fibers; (2) difference in molecular structure between UHMWPE and carbon; (3) existence of residual stress in the composite due to mismatch of thermal expansion coefficients of carbon fiber and UHMWPE; (4) poor bonding between the carbon fibers and the UHMWPE matrix; and (5) the ductile nature of the matrix itself. As a result, the carbon fiber reinforced UHMWPE orthopedic implants have been removed from the market.

Mead and Porter describe composites prepared from solid state extruded low molecular weight (58,000 or 18,400 number average molecular weight) polyethylene fibers and polyethylene matrices (both high and low density). W. T. MEAD AND R. S. PORTER, THE PREPARATION AND TENSILE PROPERTIES OF POLYETHYLENE COMPOSITES, J. APPLIED POLYMER SCIENCE, 22:3249–3265 (1978). Harpell, Kavesh, Palley, and Prevorsek made composites based on UHMWPE fibers (at least of about 500,000 molecular weight) of high tenacity and modulus, and lower molecular weight polyethylene matrices (low density, high density, and linear low density polyethylene). G. A. Harpell, S. Kavesh, I. Palley, and D. C. Prevorsek, Composite Containing Polyolefin Fiber and Polyolein Polymer Matrix, European Patent 83101731 (1983). High or ultra-high strength and-modulus UHMWPE fibers have sufficient strength and stiffness for using as reinforcement, and at the same time they possess a ductile nature. However, a composite of an UHMWPE matrix reinforced by high strength and modulus UHMWPE fibers has not heretofore been known in the art. Constraints associated with the difficulty in melt processing fibers having almost identical melting properties, with matrices may have been the reason for no prior interest in this system.

SUMMARY OF THE INVENTION

The invention provides a composite of ultra-high molecular weight polyethylene (UHMWPE) that has enhanced strength, modulus, impact strength, and creep resistance. The composite includes a polymeric matrix of UHMWPE and a reinforcement, made of UHMWPE, distributed within the matrix. The reinforcement may be selected from plies made of parallel UHMWPE fibers, short portions of UHMWPE fibers, mechanically anisotropic UHMWPE particulates, and the like, in a sufficient amount to provide the desired improvement in strength, modulus, and creep resistance.

The self-reinforced composites of the invention have several surprising features. Among these are that, unlike prior art teachings and practice, they can be cross-linked with high energy radiation such as gamma radiation and electron beam radiation to obtain improved strength and creep resistance. Further, they have improved tensile strength in a direction transverse to fibrous UHMWPE reinforcement, relative to non-filled UHMWPE, when usually a non-filled polymer is stronger than its composites in this direction. Additionally, the composites of the invention have improved impact strength, although they are filled with a high modulus material. Normally, such impact strength improvement is only seen when low modulus "rubbery" fillers are used. Also, while other composites normally achieve optimal physical properties at filler loadings of 30 wt. % or more, the composites of the invention require much less filler. The optimum range of filler addition is from about 3 to about 12 wt. % with physical properties decreasing as filler exceeds about 12 wt. %. Finally, the use of UHMWPE as a reinforcement material is necessary. When other filler materials were used, the enhancement of UHMWPE physical properties was insignificant compared to that obtained with UHMWPE reinforcement.

The composites may be sterilized using a gamma irradiation or electron beam process without the decline of physical properties experienced by non-reinforced UHMWPE and therefore may be fabricated into superior medical implants, including those implants requiring high strength, such as load bearing orthopedic implants. The composites are, of course, also useful in other medical implant applications including bone screws, bone plates, skull plates, cranial devices, fracture fixation devices, intramedullary nails, maxillofacial implants, and the like. Further, the composites do not lose their enhanced mechanical properties to any significant extent upon prolonged exposure to saline solution or body fluids, when compared to UHMWPE constructs of commercially pure polymer.

Due to the strength and impact resistance of the composites of the invention, they are well-suited to other applications demanding such materials, for example sports equipment, including, but not limited to, skis, ski poles, goggle frames, protective helmets, mountaineer's equipment, and the like, as well as specialized applications in aerospace and the like. Also, the composites may be used for external medical support such as braces of all kinds, crutches, splints, artificial limbs, and the like.

The invention also provides yet further strength-enhanced composites of UHMWPE reinforced with UHMWPE components, wherein at least some of the UHMWPE polymer of the composite matrix is cross-linked. This cross-linking may be carried out by exposure of the composite to acetylene gas under suitable conditions to allow the acetylene to penetrate the composite by diffusion and chemically react to produce cross-linked molecules.

Further, the cross-linking may be achieved by exposure to high energy radiation such as gamma or electron beam radiation. Surprisingly, irradiation by high energy produces cross-linking in such excess over bond scission or lysis that the net effect is a composite of enhanced tensile strength, elastic modulus, creep resistance, and impact strength. Further, since these irradiation treatments also sterilize the composites, they are highly suitable for use with medical implants, providing both sterilization and cross-linking in one step.

BRIEF DESCRIPTION OF THE DRAWINGS

A better understanding of the present invention can be obtained when the following detailed description of the preferred embodiment is considered in conjunction with the following drawings, in which.

DETAILED DESCRIPTION OF THE PREFERRED EMBODIMENTS

The invention composites include two necessary components: a matrix of ultra-high molecular weight polyethylene (UHMWPE) and a self-reinforcement made of UHMWPE, distributed within the matrix.

Preferably, the UHMWPE is in the form of fibers. These fibers may be present in the form of a ply, which is a sheet of fibers, wherein each fiber is aligned in a direction parallel to the other fibers. Preferably, the UHMWPE fibers have a molecular weight of at least about 1 million daltons, and up to about 5 million daltons. Commercially, such fibers may be obtained as SPECTRA 1000 and SPECTRA 900 from Allied Signal Corp. The peak melting temperature of such a fiber (measured at 10° C./min. using Thermo Analyst 2000 of TA Instruments) is at least about 140° C.

In preparing composites, the plies may be arranged so that the fibers are aligned at an angle ranging from 0° to 90° to an axis of the composite to be produced. These angles may be selected depending upon the properties that are required in the composite.

The highly oriented fibers display higher modulus and impact resistance than the matrix. The contribution of the fibers to the composite's mechanical properties depends in part on the direction of orientation of the fibers relative to an applied load. Since fibers display highest physical properties in their longitudinal direction, it is preferred to orient fibers so that the applied force acts against a longitudinal direction of the fibers. Thus, in considering a composite with an axis along which an applied load will act, the fibers may optionally be aligned parallel to the axis ("longitudinally"), at 90° to the axis ("transversely"), or at an angle between 0° and 90° to the axis ("cross-plied"). Of these orientations, the longitudinal is the most preferred and the transverse is the least preferred.

While it is normally found that other composites are weaker in tension under transverse applied forces than their matrix polymers, this is surprisingly not the case for the composites of the invention. It is theorized, without being bound, that interfacial bonding or molecular interpenetration between the UHMWPE matrix and UHMWPE reinforcement is unusually strong so that there is no resultant weakness at the polymer-reinforcement interface found in other composites.

While it is preferred that the fibers be present in the form of plies to produce composites of controlled physical properties, other types of UHMWPE reinforcement may also be used. These include fibers (not in plies), anisotropic UHMWPE particulates, short portions of UHMWPE fibers, textile constructs of UHMWPE fibers such as fabric or tape, and the like.

The matrix polymer may include any UHMWPE that has a molecular weight of preferably at least about 1 million daltons and up to about 5 million daltons. Examples of such polymers may be commercially obtained as GUR405 and GUR402 from Hoechst Celanese Corporation, as fine powders with a peak melting temperature of above 140° C. (measured in the same manner as for the fibers, explained above). Upon heating UHMWPE powder above its melting temperature, and cooling to room temperature and then reheating, melting occurs at a lower temperature, about 10° C. lower than the melting temperature of the fine powder. This thermal behavior of UHMWPE is critical in the present invention.

Preferably, the UHMWPE is processed in an inert environment since it undergoes accelerated oxidation at elevated temperatures. It should be noted that oxygen can form "transient cross-linking" in UHMWPE. Since such cross-linking is undesirable, it is preferred to perform the steps requiring heating and melting of UHMWPE in an inert environment substantially free of oxygen.

When an UHMWPE matrix resin is molded into a form of sheets or films for preparing the composite, the temperature is preferably kept below 200° C. and this temperature is preferably applied for a time less than about 5 minutes, depending upon sheet geometry. Under atmospheric pressure conditions, processing temperature should preferably not exceed 235° C., which is close to the oxidation temperature of UHMWPE, and holding time should be minimized. Higher temperatures may be used if processing is carried out under an inert gas environment. These higher temperatures also facilitate the fusion of the composites under laminating conditions.

Generally, composites of the invention are produced by filling a matrix polymer with fibers in the range from about 1 to about 20 wt. %, based upon the weight of the reinforcement and the matrix polymer. Preferably, the composites contain from about 3 to about 12 wt. % reinforcement. This is in stark contrast to the art which generally teaches loading with reinforcement at levels of 30% or more. Here, contrary to the art's general teaching, it has been found that the UHMWPE composites of the invention with the best physical properties have from 3 to 12 wt. % reinforcement. Indeed, using more than about 12 wt. % reinforcement causes a decline in properties of the composites of the invention, although they are still useful with up to about 30 wt. % reinforcement. When other organic fibers, like nylon-6 and polyethylene terephthalate (PET) fibers, have been incorporated into UHMWPE, at 3–10% fiber loading, the resultant composites have shown very limited improvements in UHMWPE properties. Further, the composite physical properties were found to worsen after aging in 37° C. water.

In general, layers or mixtures of polymer matrix and reinforcement are processed at about 130° C., under moderate pressure ranging from about 4 to about 12 MPa to produce the composite of the invention.

To reduce the melting temperature of the UHMWPE matrix, virgin UHMWPE powder is first melted and pressed into sheets or films in a mold, such as a rectangular metal frame with an upper and lower steel pressing plate. Pressing is carried out under conditions that cause the UHMWPE powder to melt and form a sheet or film of UHMWPE. Such conditions will vary depending upon film thickness and UHMWPE melting point. For a 0.025–0.035 inches thick film, this pressing is preferably carried out at a temperature of from about 150° to about 220° C., more preferably 175° C.; and preferably under a pressure of from about 2 to about 13 MPa, more preferably about 7 MPa, for about 3 minutes. Clearly, temperature and time are dependent on sheet geometry, especially thickness.

As an alternative, sheets or films of the matrix polymer may be produced by melt crystallizing UHMWPE powder under pressure of preferably less than about 2 MPa. The resultant sheets or films are porous, which facilitates melt diffusion when the composite is assembled.

When laminating the composites, it is preferable to apply pressure when the temperature reaches the required level. During lamination, the sheets of polymeric matrix and reinforcement are heated up to a temperature and for a time so that the film is able to melt at least partially to then coat the reinforcement so that a unitary solid is produced upon cooling. Typically, for a 6 mm thick composite, the polymer film-reinforcement construct is heated to about 135° C. and subjected to pressures ranging up to about 6 MPa for about 30 minutes. During the lamination of the composite, when plies or longitudinal fibers of UHMWPE form the reinforcement, it is preferable to apply axial tension to the fibers to avoid molecular chain relaxation at high temperatures and thereby prevent non-uniform contraction of the fibers. Preferably, such composites should be removed from the mold when the mold temperature has dropped to below 70° C., more preferably below 40° C.

Composites according to the invention may be sterilized under an ethylene oxide atmosphere if no cross-linking reactions are desired, or in the alternative, with high energy radiation, preferably gamma, x-ray, or electron beam radiation. As explained above, such high energy radiation also cross-links the UHMWPE composites of the invention and unexpectedly enhances certain physical properties. Preferably, this radiation is applied when the composite is in an acetylene-containing environment to enhance cross-linking. Therefore, the composites are eminently suitable for use in the fabrication of constructs for high strength, high impact use, including sports equipment, protective equipment, and the like. UHMWPE is biocompatible and provides high strength and high modulus. Composites according to the invention have enhanced physical properties relative to non-reinforced UHMWPE and do not suffer significant deterioration in physical properties when subjected to saline solutions at 37° C. for prolonged periods of time. Further, composites of the invention have increased creep resistance, a critical short-coming in current UHMWPE constructs. Thus, the composites of the invention are highly suitable for use in medical implants, including load-bearing prosthetic implants, and the like.

As used in the specification and claims, the term "medical implants" includes all those devices that are implantable into living bodies to provide for augmentation, support, repair, or reconstruction of body tissue, especially bone.

In a further application, the composites of the invention can be used to fabricate components of medical appliances. The term "medical appliances" refers to externally worn or used devices, or components thereof, that brace or support a living body, including, but not limited to, knee braces, back braces, crutches, cervical collars, and the like.

When composites according to the invention are subjected to an acetylene gas environment, under conditions that will allow diffusion of the acetylene into the composite, the acetylene reacts with at least some of the UHMWPE to produce cross-linking. Thus, by judicious selection of acetylene soaking time, temperature, and pressure, a desired level of crystallinity may be obtained in a composite. Such cross-linking further enhances the strength and creep resistance of the composite.

The following examples are illustrative of the invention and do not limit the scope of the invention as described above and claimed below.

Example 1

The materials used in Example 1 are UHMWPE resin as matrix (trade name GUR405 from Hoechst Celanese Corporation, U.S.A.) supplied as a virgin fine powder, and high strength and modulus UHMWPE fiber as reinforcement (trade name SPECTRA 1000 from Allied Signal Corporation, U.S.A.). The UHMWPE powder cannot be used directly in making composites because its melting point temperature is very close to that of the fiber so that fibers might also melt. To reduce the intended matrix polymer's melting temperature, the UHMWPE powder was first melted and the molten polymer then pressed into sheets in a metal frame between two stainless steel plates at a temperature of about 180° C. and a pressure of about 7 MPa for 3 minutes. The resulting sheet dimensions were 12 cm×9 cm×0.025 cm (weighing about 3 grams) and 12 cm×9 cm×0.035 cm (weighing about 4 grams).

SPECTRA 1000 fibers were wound twice onto a metal frame, which has a thickness less than that of the expected composite, to obtain four layers of fibers. Five UHMWPE sheets were arranged, one each of thickness 0.035 cm on top and at the bottom, and three of thickness 0.025 cm between each fiber layer. The resulting construct polymer-fiber was melted and molded into a composite by pressing between two stainless plates at the temperature of about 130° C. and pressure of about 6 MPa for about 10 minutes then cooled under pressure in a CARVER Laboratory Press (Model C). The composite was taken out of the mold after the temperature dropped below 60° C. (If no forced cooling is used, then it takes about 3 hours for the temperature to drop below 60° C.) The composite, which can be represented by a laminate code of $[/^0/^0/^0/^0]_t$ (where "0" represents the angle of orientation of a layer of fibers and "/" a layer of matrix), had a dimension of about 12 cm×9 cm×0.15 cm, and a fiber loading of 4% by weight, with a very fine surface finish, which is dependent on the roughness of the pressing metal plates used.

Example 2

Following the same procedure as in Example 1, a cross-ply composite $[/^0/^{90}/^{90}/^0/]_t$ with a fiber loading of 4% was obtained by winding the fiber onto the metal frame so that two layers are in a 90° direction and two layers in 0° direction relative to an axis of the composite.

Example 3

UHMWPE sheets were obtained by first melt-processing the UHMWPE powder (of Example 1) without applied pressure between two stainless plates at about 180° C. for about 3 minutes in a Carver Laboratory Press. The resulting polymer sheets were porous. When making composites, these porous sheets diffuse and bond together more easily than those of Examples 1 and 2. Thus, it is preferred to make polymer sheets this way. The other procedures for making composites are the same as in Examples 1 and 2. It is expected that the bonding of polymers to fibers according to this example would be better than those in Examples 1 and 2, although tests were not performed to characterize interfacial strength between matrices and fibers, due to the difficulty of measuring this property.

Films made under less than 2 MPa pressure will provide a facile melt diffusion during assembly and hence maximize adhesion between fiber and polymer. This maximizing of adhesion beneficially affects physical properties. Thus, contrary to expectation, tensile strength in the transverse direction is higher than for unfilled UHMWPE, a characteristic which is not found in other composites.

Composites with various stacking sequence (fiber orientation) and fiber loadings were made for mechanical testing. Dogbone tension specimens were cut from the composite sheets (in both longitudinal and transverse directions) using a metal die and tensile strength was tested on the specimens on an INSTRON universal mechanical tester. The results (average of at least 5 specimens for each case) are summarized in Table 1. Also included in Table 1 are the results for the non-reinforced UHMWPE samples (made and tested under the same conditions as for the composite), for the purpose of comparison. Compared with the non-reinforced UHMWPE, the composites have greater yield strength and relative modulus in the longitudinal direction and showed almost no change in transverse direction. Small increases of strength and stiffness in the transverse direction indicate a good interfacial bonding. Cross-ply laminates also showed superior properties.

TABLE 1

Tensile Property of GUR405 and Its Composites ($V_f$ = ~5.5 wt. %)

| Sample | Yield Stress, MPA | Failure Stress, MPa | Modulus, MPa |
|---|---|---|---|
| GUR405 sheet | 24.7 | 47.9 | 578 |
| $[/0/0/0/0/]_t$ | 117.1 | 40.2 | 2652 |
| $[/90/90/90/90/]_t$ | 24.7 | 35.9 | 694 |
| $[0/90/90/0/]_s$ | 56.7 | 41.5 | 1524 |

Example 4

Following the same procedure as in Example 3, a composite with a thickness of greater than 5 mm was obtained by using 17 layers of processed UHMWPE sheets and 16 layers of fibers. The typical stacking sequence was $[^0/^{90}_2/^0_2/^{90}_2/^0]_s$. The composites had a very fine surface finish and a fiber loading of 5% by weight.

Example 5

Following the same procedure as in Example 3, composites with stacking sequences of $[/^0/^0/^0/^0/]_t$ and $[/^{90}/^{90}/^{90}/^{90}/]_t$ were assembled. Each composite had a fiber loading of 5 wt. %. Gamma irradiation of the composites was conducted using a dose of 2.50 Mrads in three different gas environments, namely, air, nitrogen (practically pure), and acetylene. For each condition, 5 specimens were used.

Two ground-jointed separatory funnels, each with 15 specimens inside for each case, were sterilized in the nitrogen and acetylene environments, respectively. The purge cycles were as follows: evacuate separatory funnel containing samples; purge nitrogen or acetylene; evacuate separatory funnel again; purge nitrogen or acetylene once more.

The duration for each step was about 15 minutes. A total of four cycles was used. Finally, the separatory funnel was sealed and no gas exchange occurred. For acetylene gas the pressure inside separatory funnel had a gauge reading of about 2.0 psi, and for nitrogen gas the pressure inside was just above atmospheric pressure. Irradiation was done normally after at least 3 days so that the gases could diffuse into the samples.

Gamma irradiation was completed in a gamma irradiator using $^{60}$Co isotopes as a source. All irradiations were done at room temperature. Following gamma irradiation, a tensile test was run on the specimens on an INSTRON universal mechanical tester (Model 1125) at room temperature using a loading velocity of 20 mm/min. Gauge length was 20 mm and the entire testing was run under computer control. All the mechanical tests were run within three weeks after exposure to gamma radiation.

The results are illustrated in FIGS. 6–9 from which it can be understood that gamma irradiation sterilization in acetylene-containing environment is preferred.

Example 6

Figure 1:
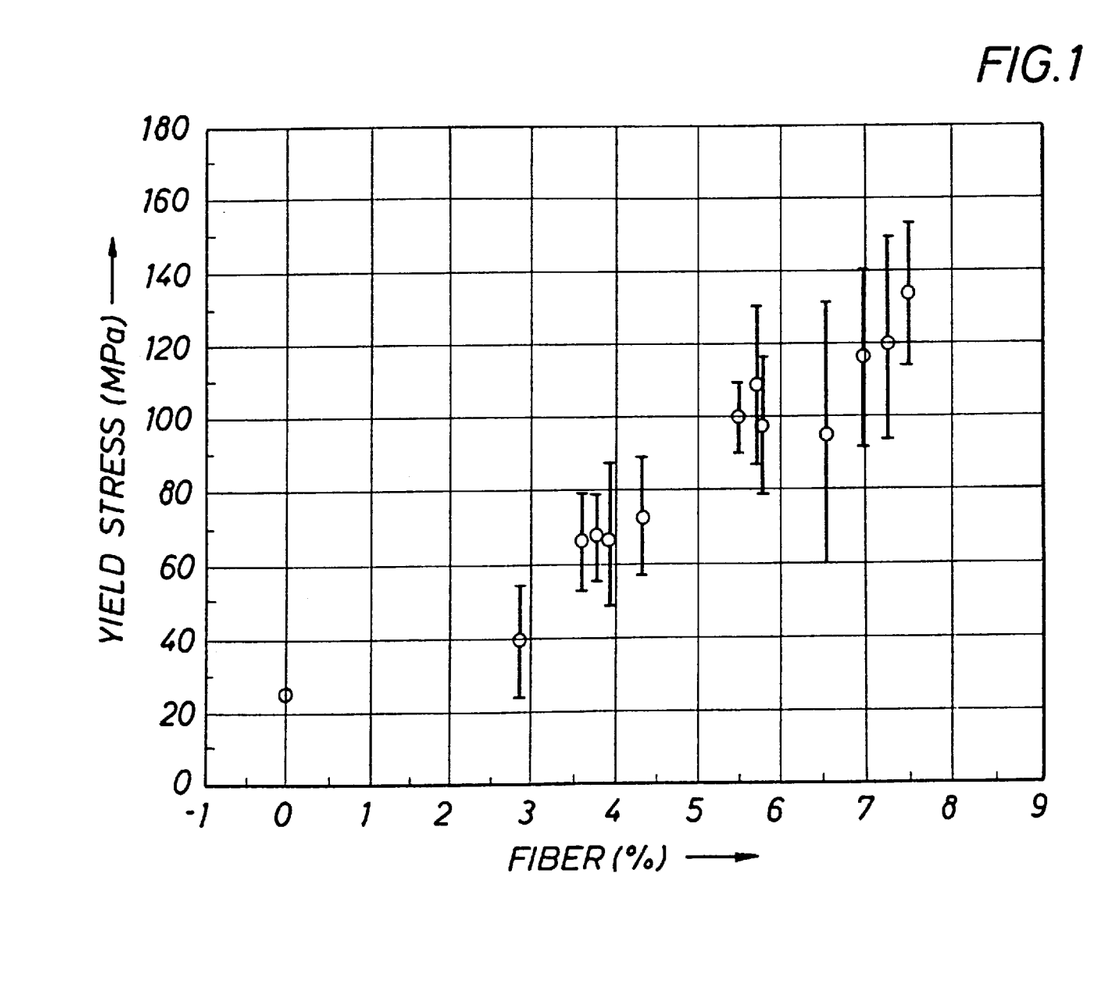
FIG. 1 is a graphic depiction of tensile yield strength versus percent fibers for composites of the invention.
Figure 2:
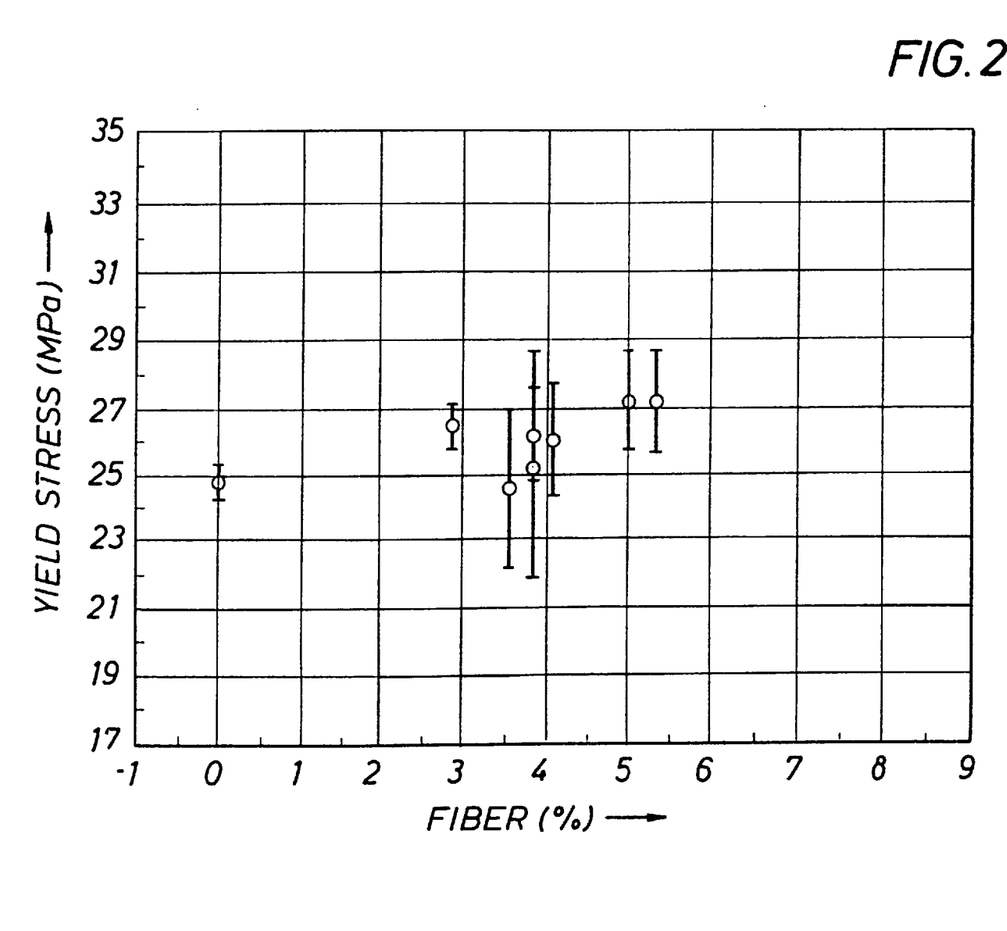
FIG. 2 is a graphic representation of tensile yield strength versus percent fibers for unidirectional composites of the invention.
Figure 3:
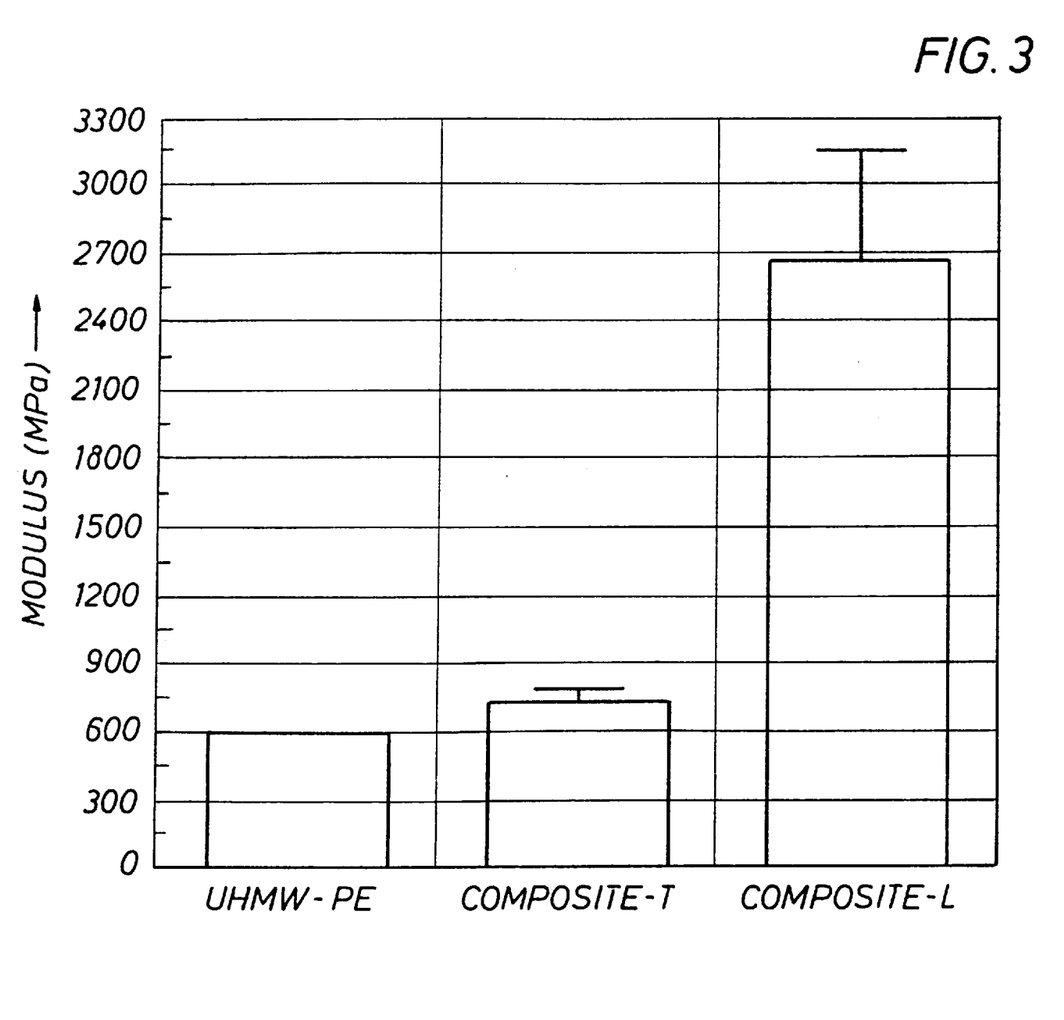
FIG. 3 is a graphic representation of the tensile modulus of ultra-high molecular weight polyethylene as compared to composites according to the invention.
Figure 4:
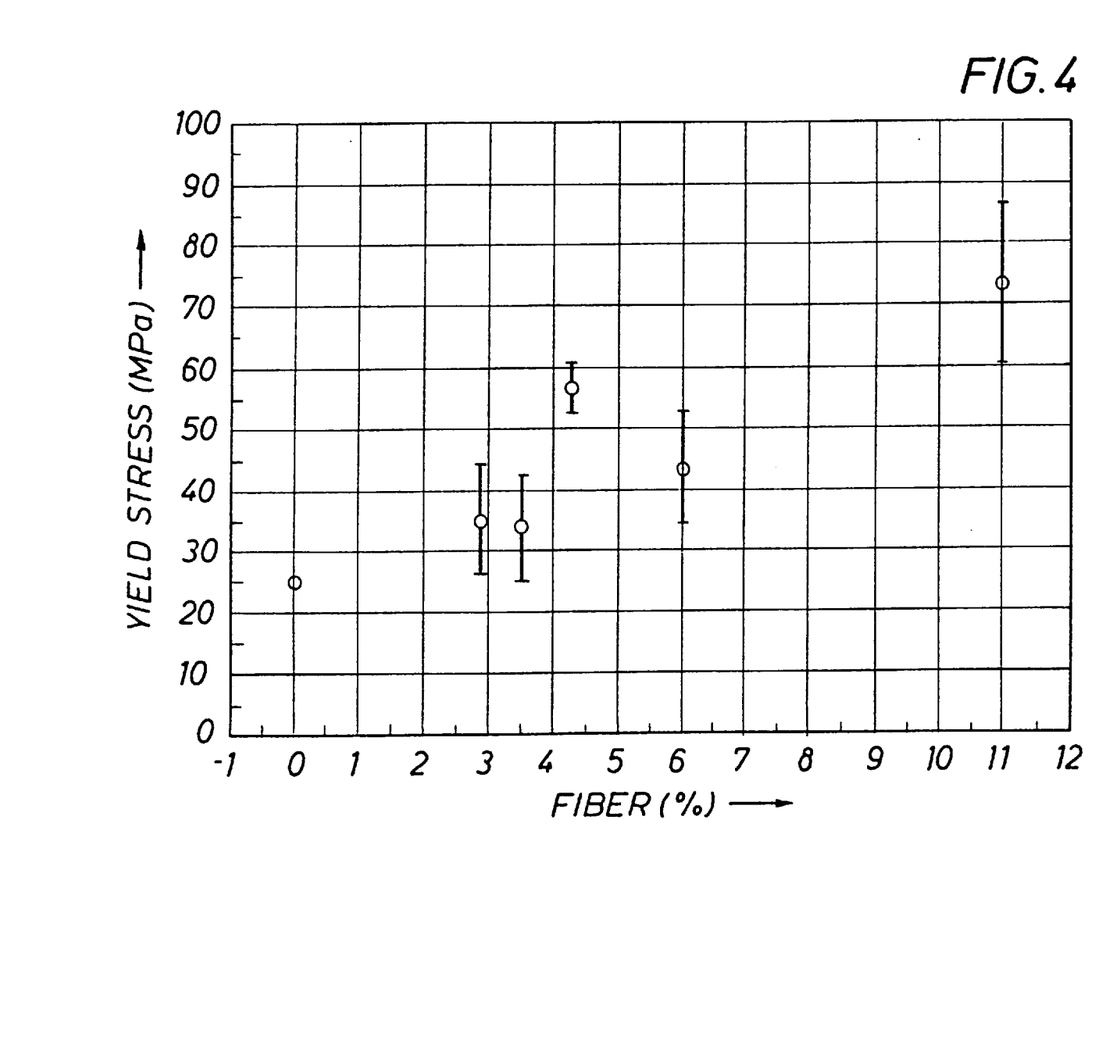
FIG. 4 is a graphic depiction of tensile yield strength of cross-ply composites versus percent fiber for composites according to the invention.
Figure 5:
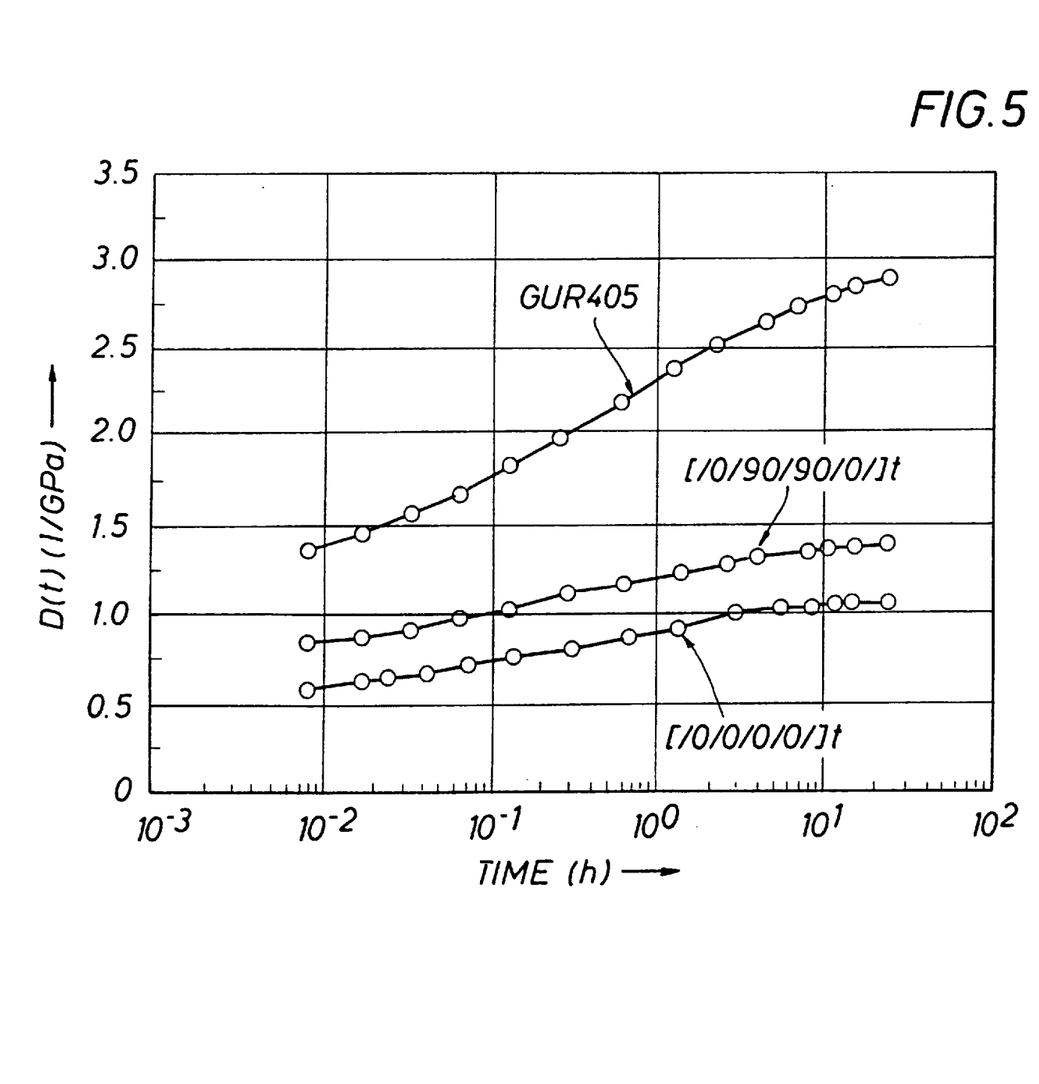
FIG. 5 is a graphic depiction of tensile creep over time at room temperature under a 5 MPa stress for ultra-high molecular polyethylene as a control and composites according to the invention.
Figure 6:
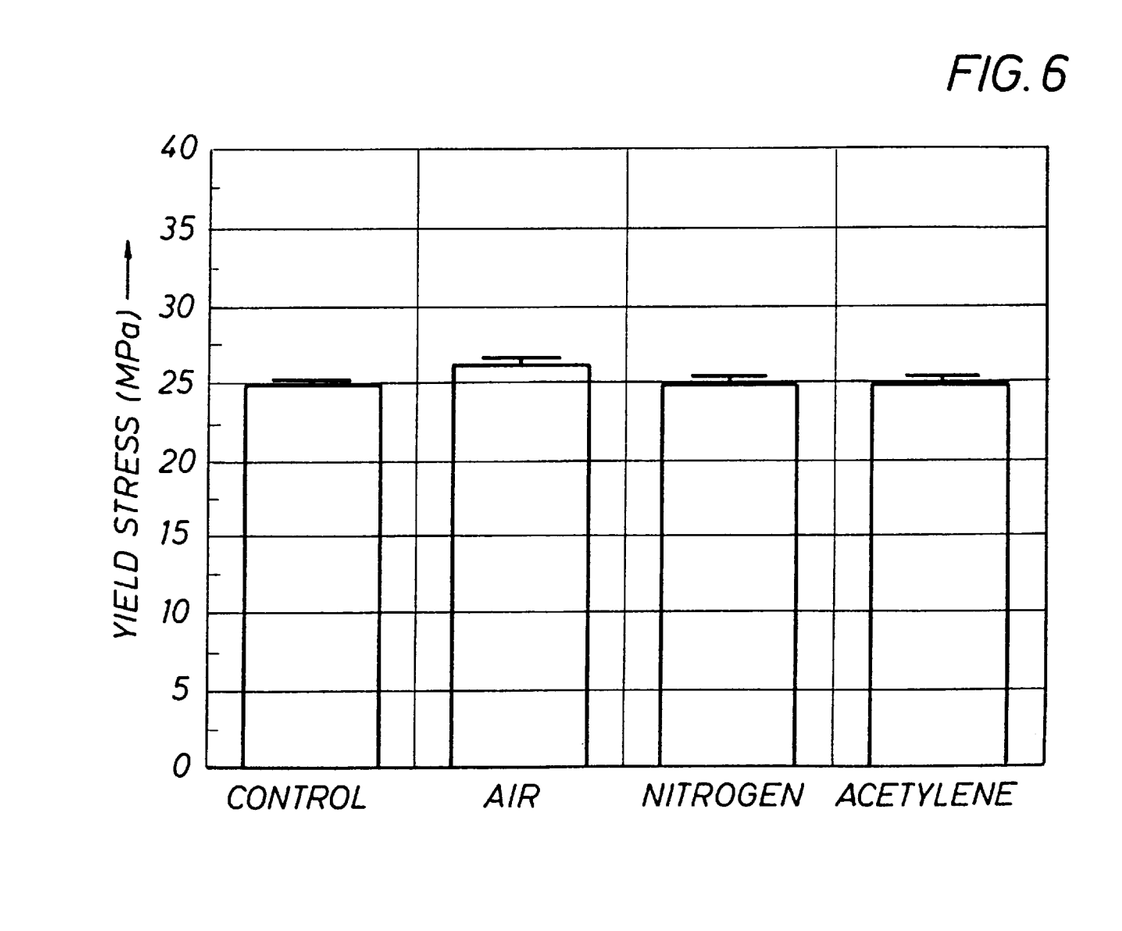
FIG. 6 is a graphic depiction of the effect of a 2.50 Mrad dose of gamma radiation on the tensile stress of a control and ultra-high molecular weight polyethylene composites of the invention in an environment of air, nitrogen, or acetylene.
Figure 7:
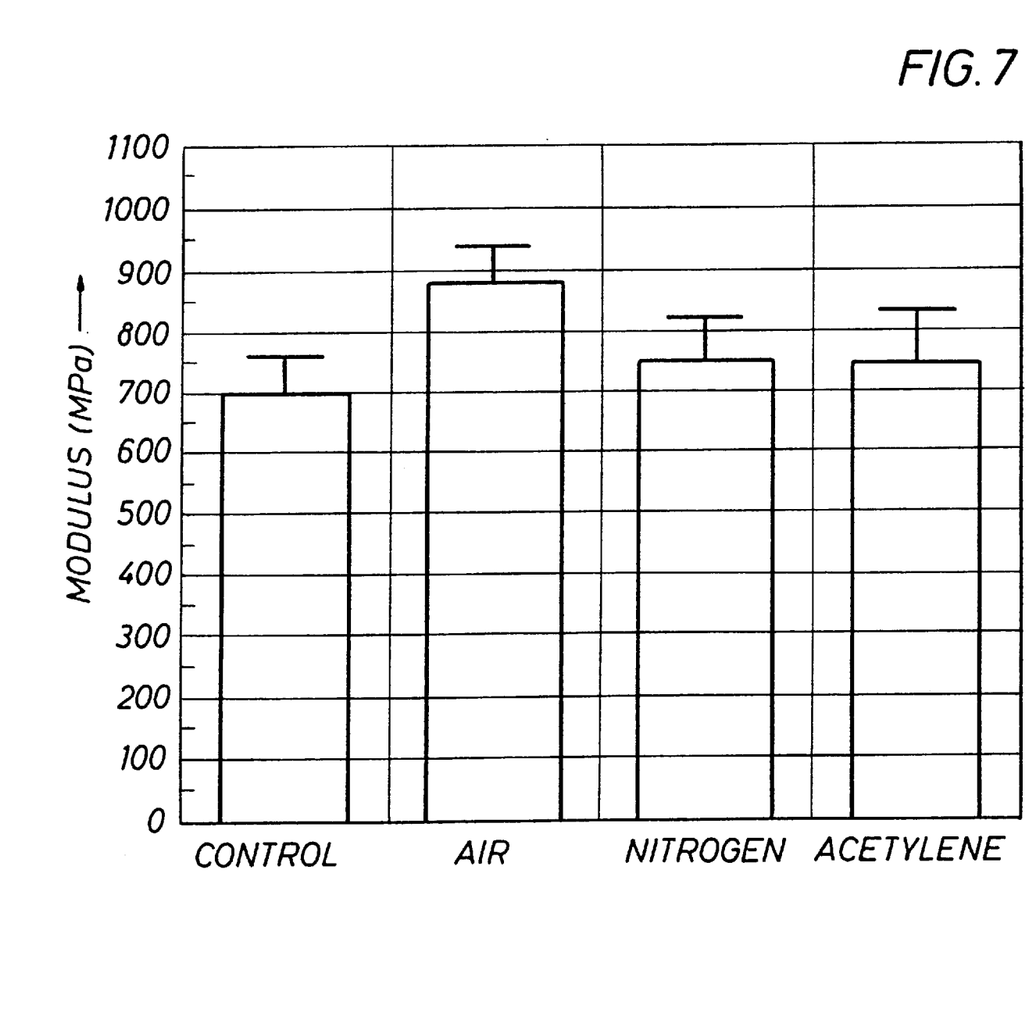
FIG. 7 is a graphic depiction of the tensile moduli of gamma-irradiated unidirectional composites as compared to a control of ultra-high molecular weight polyethylene.
Figure 8:
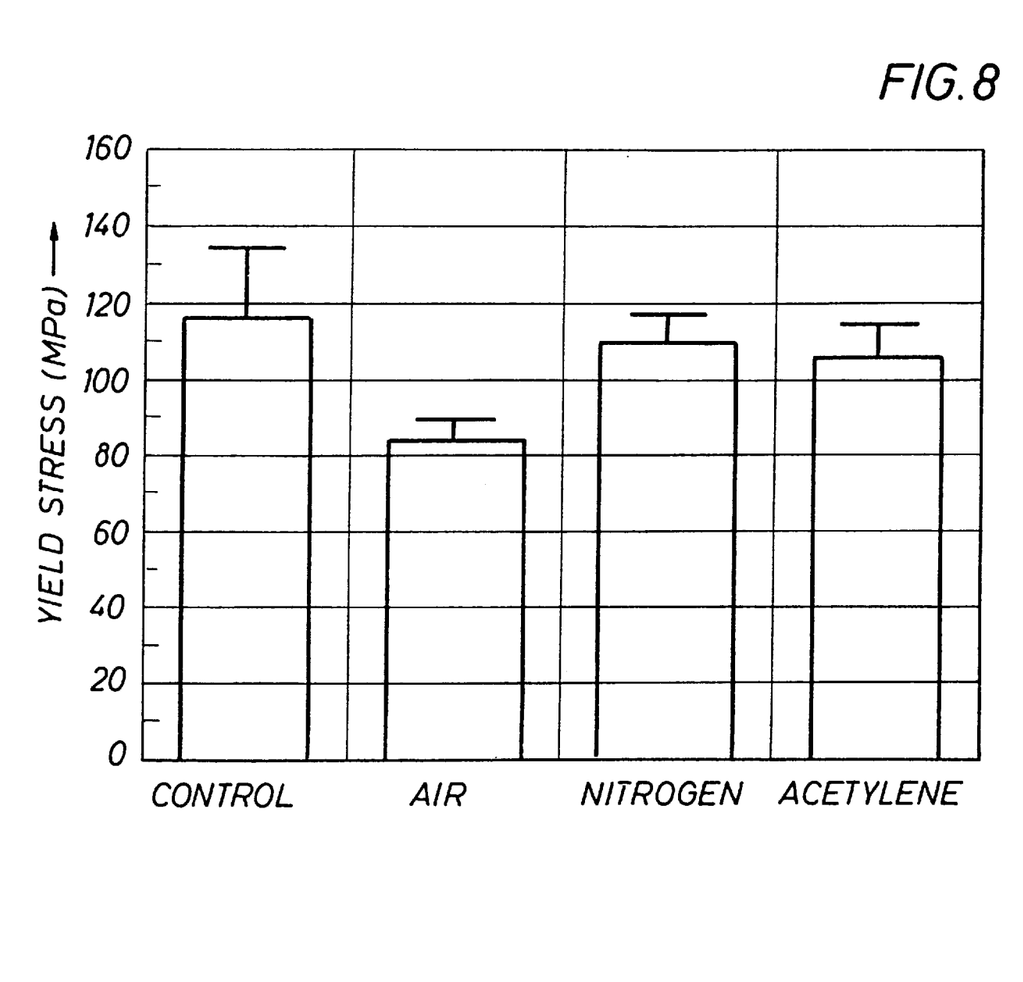
FIG. 8 is a graphic depiction of the tensile yield strength of gamma-irradiated unidirectional composites along the fiber axis as compared to a control of ultra-high molecular weight polyethylene.
Figure 9:
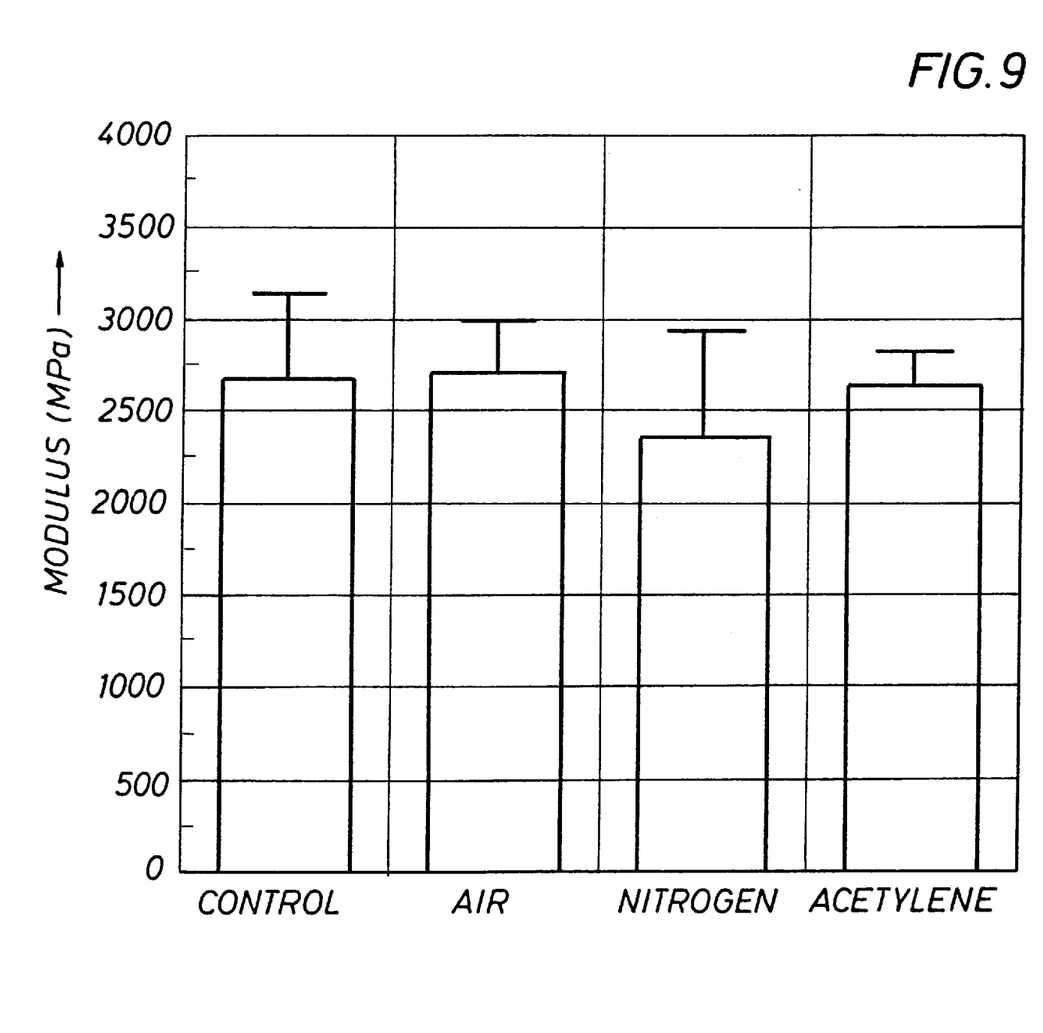
FIG. 9 is a graphic depiction of the tensile modula of gamma-irradiated unidirectional composites taken along the fiber axis, as compared to a control of UHMWPE.

Following the same procedure as in Example 3, composites with stacking sequences of $[/^0/^0/^0/^0/]_t$ and $[/^0/^{90}/^{90}/^0/]_t$ were assembled. Each composite had a fiber loading of 5 wt. %. A constant load creep test was run on the composites and GUR405 polymer as a control. Table 2 lists the compliances of the 24-hour room temperature creep tests. The superior creep-resistance of composites over the non-reinforced UHMWPE control can be seen from this table or from the compliance versus time plot in FIG. 5.

TABLE 2

Creep Compliance after 24 Hours at 5 MPa

| Sample | Compliance (1/GPa) |
|---|---|
| GUR405 sheet | 2.89 |
| [0/0/0/0/]$_t$ | 1.05 |
| [0/90/90/0/]$_t$ | 1.14 |

Example 7

Following the same procedure as in Example 3, cross-ply composites were assembled. Each composite had a fiber loading of 4.2 wt. %. Composites were gamma sterilized at a dose of 2.50 Mrads in air. Double-razor notch izod impact tests were performed on the composites, and also on plain UHMWPE for comparison. Table 3 lists the results.

TABLE 3

Double-Razor Notch Load Izod Impact Test Results

| Sample | γ-Sterilized | Notch/Fiber Orientation | Strength (Ft-lb/in$^2$) |
|---|---|---|---|
| GUR405 sheet | No | N/A | 55 ± 0 |
|  | Yes | N/A | 44 ± 1 |
| [//0/90/0/90/0/90/0/90/0/]$_s$ | Yes | Notch between fibers | 53 ± 2 |
|  | Yes | Notch along fibers | 47 ± 6 |
| [//90/0/90/0/90/0/90/0/]$_s$ | Yes | Notch between fibers | 59 ± 2 |
|  | Yes | Notch along fibers | 51 ± 2 |

From this data, it is apparent that unfilled UHMWPE loses about 20% of strength on exposure to gamma radiation. However, such strength loss is surprisingly not found in the composites which instead show strength improvement by about 7 to about 30% due to reinforcement. Also, while filling with rubbery, low modulus fillers is known to improve impact strength, here surprisingly, composites filled with high modulus fibers have improved impact strength.

Although the invention has been described with reference to its preferred embodiments, those of ordinary skill in the art may, upon reading this disclosure, appreciate changes and modifications which may be made and which do not depart from the scope and spirit of the invention as described above and claimed below.

What is claimed is:

1. A composite of high tensile and impact strength, elastic modulus, and creep resistance, the composite comprising:

an essentially non-oriented matrix of an ultra-high molecular weight polyethylene polymer; and a reinforcement of ultra-high molecular weight polyethylene dispersed in and bonded to said matrix in sufficient amount to increase the tensile and impact strength, elastic modulus, and creep resistance of the composite above the tensile and impact strength, elastic modulus, and creep resistance of non-reinforced ultra-high molecular weight polyethylene matrix polymer, the reinforcement comprising up to about 12 percent by weight of the composite, the reinforcement selected from the group consisting of fibers, plies of fibers, and textile constructs;

wherein a unidirectionally reinforced segment of the composite exhibits a transverse strength equal to or greater than the strength of a non-reinforced ultra-high molecular weight polyethylene matrix polymer of substantially similar dimensions.

2. The composite of claim 1, wherein at least some of the matrix ultra-high molecular weight polymer is cross-linked.

3. The composites of claim 1, wherein the composite is sterilizable by a process comprising exposure to gamma irradiation.

4. The composite of claim 1, wherein the composite is sterilized and cross-linked, said sterilization and cross-linking produced by a process comprising exposing the composite to high energy radiation in the presence of an acetylene-containing environment.

5. The composite of claim 1, wherein impact strength of the composite after irradiation with a high energy beam of radiation is greater than impact strength of unreinforced ultra-high molecular weight polyethylene of the matrix polymer subjected to the same radiation.

6. A composite structure of self-reinforced ultra-high molecular weight polyethylene comprising:

an at least partially cross-linked, essentially non-oriented, matrix of an ultra-high molecular weight polyethylene polymer; and a reinforcement of ultra-high molecular weight polyethylene polymer dispersed in and bonded to said matrix in sufficient amount to increase the tensile and impact strength, elastic modulus, and creep resistance of the composite above the tensile and impact strength, elastic modulus, and creep resistance of non-reinforced ultra-high molecular weight polyethylene matrix polymer, the reinforcement comprising up to about 12 percent by weight of the composite, the reinforcement selected from the group consisting of fibers, plies of fibers, and textile constructs;

wherein a unidirectionally reinforced segment of the composite exhibits a transverse strength equal to or greater than the strength of non-reinforced ultra-high molecular weight polyethylene matrix polymer of substantially similar dimensions.

7. The composite structure of claim 6, wherein the cross-linking is produced by a process comprising exposing the structure to high energy radiation in an acetylene-containing environment.

* * * * *